(12) United States Patent
Wagner et al.

(10) Patent No.: US 11,215,575 B2
(45) Date of Patent: Jan. 4, 2022

(54) HAND HELD MOISTURE METER INTELLIGENT RECORDING

(71) Applicant: Wagner Electronic Products, Inc., Rogue River, OR (US)

(72) Inventors: Eric Wagner, Rogue River, OR (US); Shawn Gerber, Grants Pass, OR (US)

(73) Assignee: Wagner Electronic Products, Inc., Rogue River, OR (US)

( * ) Notice: Subject to any disclaimer, the term of this patent is extended or adjusted under 35 U.S.C. 154(b) by 160 days.

(21) Appl. No.: 16/653,412

(22) Filed: Oct. 15, 2019

(65) Prior Publication Data

US 2020/0132615 A1   Apr. 30, 2020

Related U.S. Application Data

(60) Provisional application No. 62/753,681, filed on Oct. 31, 2018.

(51) Int. Cl.
*G01N 27/22* (2006.01)
*G01D 18/00* (2006.01)

(52) U.S. Cl.
CPC ......... *G01N 27/223* (2013.01); *G01D 18/004* (2013.01); *G01D 18/008* (2013.01); *G01N 27/226* (2013.01)

(58) Field of Classification Search
CPC ... G01N 27/226; G01D 18/008; G01D 18/004
See application file for complete search history.

(56) References Cited

U.S. PATENT DOCUMENTS

| 5,402,076 A * | 3/1995 | Havener | G01N 22/04 324/689 |
| 5,568,747 A * | 10/1996 | Lloyd | G01N 27/121 324/694 |
| 7,142,123 B1 * | 11/2006 | Kates | G01N 27/048 340/602 |
| 2003/0169054 A1 * | 9/2003 | Rynhart | G01N 27/223 324/649 |
| 2008/0262752 A1 * | 10/2008 | Cai | G01N 23/083 702/40 |
| 2012/0234078 A1 * | 9/2012 | Hagi | G01N 27/223 73/29.02 |

* cited by examiner

*Primary Examiner* — Alvaro E Fortich
(74) *Attorney, Agent, or Firm* — Klarquist Sparkman, LLP

(57) ABSTRACT

Methods and apparatus are disclosed for automated acquisition of moisture readings using a handheld moisture meter. In automated mode, a succession of moisture content readings at successive positions can be acquired without any user interface input, by moving the moisture meter to successive positions on a sample, and holding steady at each position. Moisture readings stable for a time period (e.g. one second) are indicative of moisture content of a sample at a stationary position and are collected. Moisture readings varying in time are indicative of motion of the moisture meter and are not collected. Statistics can be performed on the collected readings. Notifications of stable readings and alerts for out-of-range readings can be provided. Hardware and software architectures are disclosed. The innovative technology is suitable for wood, concrete, and other materials at any stage of manufacturing or product lifecycle.

19 Claims, 9 Drawing Sheets

HAND HELD MOISTURE METER INTELLIGENT RECORDING

CROSS REFERENCE TO RELATED APPLICATION

This application claims the benefit of U.S. Provisional Application No. 62/753,681, entitled "HAND HELD MOISTURE METER INTELLIGENT RECORDING," filed Oct. 31, 2018, which application is incorporated by reference herein in its entirety.

FIELD

This application describes the invention of the process of automatically recording measurements using a handheld moisture meter.

BACKGROUND

Moisture measurements can be important for quality control at various stages of manufacture of wood products, and also subsequently during their operational life. Moisture measurements are also important is assessing condition of other materials such as concrete, drywall, paint, sand, or soil. It can often be desirable to perform multiple spot measurements over the spatial extent of a product or material sample to better assess the overall moisture condition. Handheld moisture meters can be convenient for making such measurements, but acquisition and analysis of multiple measurements can become tedious. Accordingly, there remains a need for improved technology for acquiring multiple moisture measurements with a handheld moisture meter.

SUMMARY

In summary, the detailed description is directed to various innovative technologies for performing moisture measurement with a handheld moisture meter. Some examples of the disclosed technology support automatic determination of when a reading should be taken, when a reading should be retained or discarded, when a moisture meter has been moved, and/or automatic computation of various statistical measures on acquired moisture readings, in varying combinations.

In certain examples, the disclosed technology can be implemented as a computer-implemented method performed by a moisture meter. An automatic recording mode is entered in response to a received input. In the automatic recording mode, the following actions are performed without further user input at a user interface. A first stable moisture reading is detected for a predetermined period of time. Subsequently, a varying moisture reading is detected that is different from the first stable moisture reading. Then, after the varying moisture reading, a second stable moisture reading is detected, which is stable for the predetermined period of time. The first and second stable moisture readings are stored.

In some examples, the method can extend to detecting and storing additional stable moisture readings while in the automatic recording mode, and computing one or more statistics on the first, second, and additional stable moisture readings. The statistics can include one or more of: minimum, maximum, arithmetic mean, or standard deviation. A second received input can clear the statistics, while the moisture meter remains in the automatic recording mode. In additional examples, only moisture above a threshold can be incorporated into the computed statistics. A third received input can cause the moisture meter to exit the automatic recording mode.

In further examples, the automatic recording mode can include making repetitive periodic raw measurements indicative of moisture near the moisture meter, and processing the raw measurements to obtain a succession of moisture readings including stable and varying moisture readings. The processing can include one or more of: averaging, filtering, or rounding. The repetitive measurements and processing can be performed continually during the automatic recording mode, without any user input. A varying moisture readings can differ from a respective immediately preceding moisture reading by at least a threshold amount.

In additional examples, a stable moisture reading can be compared with a first threshold or a second threshold, and an alert signal can be generated if the first stable moisture reading is below the first threshold or above the second threshold. Notification signals can be generated upon detection of a stable moisture reading or upon detection of a varying moisture reading.

In certain examples, the disclosed technology can be implemented as a moisture meter apparatus. The moisture meter includes an electronic moisture sensor and one or more processors configured to operate the moisture sensor and communicate with a user interface. The processors are configured to execute first, second, and third instructions. Execution of the first instructions causes the moisture meter to acquire a succession of stable moisture readings in a repetitive loop without input from the user interface. Each stable moisture reading is unchanging for at least a predetermined time duration. Successive pairs of stable readings are separated by at least one varying moisture reading different from an immediately preceding stable moisture reading. The varying moisture readings can be indicative of movement of the moisture meter. The second instructions are for computing statistics on the succession of stable moisture readings. The third instructions are for providing the statistics to the user interface.

In some examples, the user interface can include a keypad and a display on the moisture meter, while in other examples, the user interface can be part of a computing device coupled to the moisture meter over a network.

In certain examples, the disclosed technology can be implemented as a method. An input is provided at the user interface of a moisture meter, to place the moisture meter into an automatic recording mode. Then, in the automatic recording mode, the moisture meter is placed at successive positions on a sample to acquire a succession of stable moisture readings without further input at the user interface.

In some examples, the moisture readings are considered stable if they vary by less than a threshold amount over a predetermined time duration. In additional examples, a pass-fail determination for the sample can be made, based on the acquired stable moisture readings. The sample can be wood or concrete, or other materials.

The innovations can be implemented as part of one or more methods, as part of one or more instruments or computing systems adapted to perform an innovative method, or as part of non-transitory computer-readable media storing computer-executable instructions for causing an instrument or computing system to perform the innovative methods. The foregoing and other objects, features, and advantages of the invention will become more apparent from the following detailed description, which proceeds with reference to the accompanying figures.

DETAILED DESCRIPTION

Introduction

Handheld moisture meters can be used by placing the meter on a surface of a sample to determine sample moisture within a certain penetration depth, at the location where the meter is placed. Because the measurement is local, and because moisture content of samples can vary across their dimensions, it can be desirable to obtain moisture content readings at a number of locations on the sample surface so as to determine the condition of the sample with confidence. However, requiring an operator to press a key or provide similar input every time a measurement is to be taken can become tedious, can contribute to operator fatigue, and can lead to non-compliance or an increased rate of operator error. The disclosed technologies provide an automated recording mode, in which a moisture meter can record a stable reading when the meter is held in a fixed position on a sample. The moisture meter can also detect variable readings when the meter is moved, and can be ready to take another reading when the moisture reading stabilizes at a new fixed position. Methods and apparatus for these technologies are described further herein.

Example Moisture Meter

Figure 1:
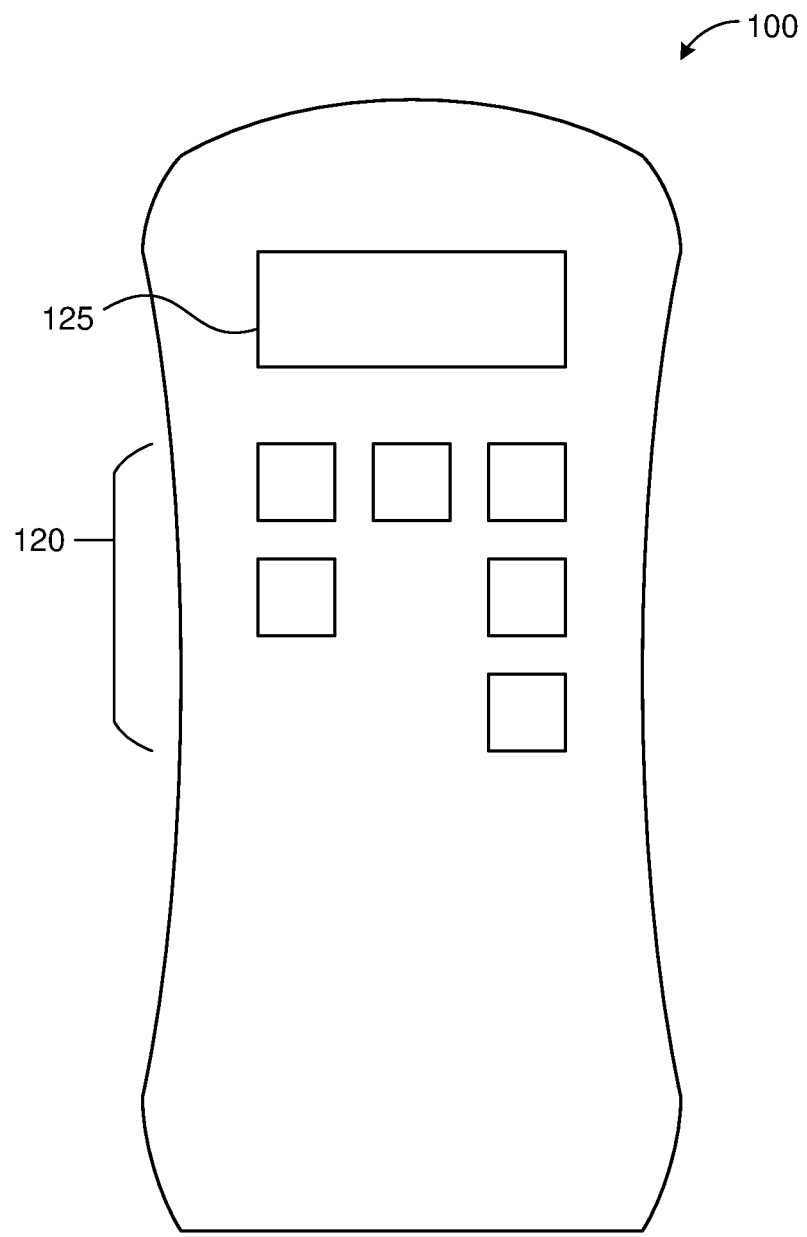
FIG. 1 depicts a top view of an example handheld moisture meter suitable for implementing disclosed technologies.

FIG. 1 depicts a top view of an example handheld moisture meter 100 suitable for use with disclosed technologies. Meter 100 can have a size and weight suitable to be held in a user's hand. One or more moisture sensors (not shown) can be placed on or near a bottom surface of the meter 100. One or more moisture readings can be taken with the bottom surface of the moisture meter placed in contact with a sample whose moisture is to be measured.

The top surface can accommodate a keypad 120 comprising a plurality of keys which can be touch-sensitive keys, proximity-sensitive keys, or pushbuttons. The top surface can also include a display 125, which can be a segmented display, a pixelated screen, or can include one or more annunciators for specific functions. The functions of display 125 and keypad 120 can be integrated, for example as a touchscreen keypad, or as one or more softkeys in which a current function of a key of keypad 120 is indicated on the display 125.

Example Usage of Moisture Meter

Figure 2:
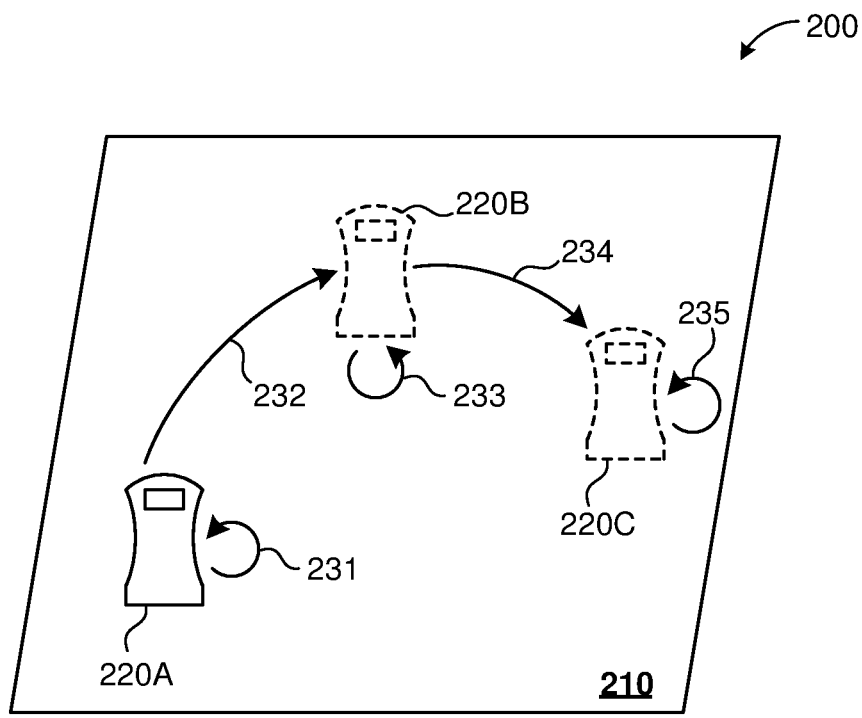
FIG. 2 depicts example usage of the disclosed technologies.

FIG. 2 depicts example usage of the disclosed technologies. A handheld moisture meter is shown at three successive positions 220A-220C on a sample 210, which can be wooden board. Arrows 232, 234 indicate the moisture meter being moved, either along the surface of sample 210, or off the surface—i.e. by picking up the moisture meter and repositioning at the next location 220B, 220C. At each of these positions 220A-220C, the meter can be held stationary as indicated by arrows 231, 233, 235 and respective moisture readings can be acquired automatically without user input. The moisture meter can beep when a reading has been recorded, indicating that the user can move the meter to another location.

Example Use Case

Figure 3:
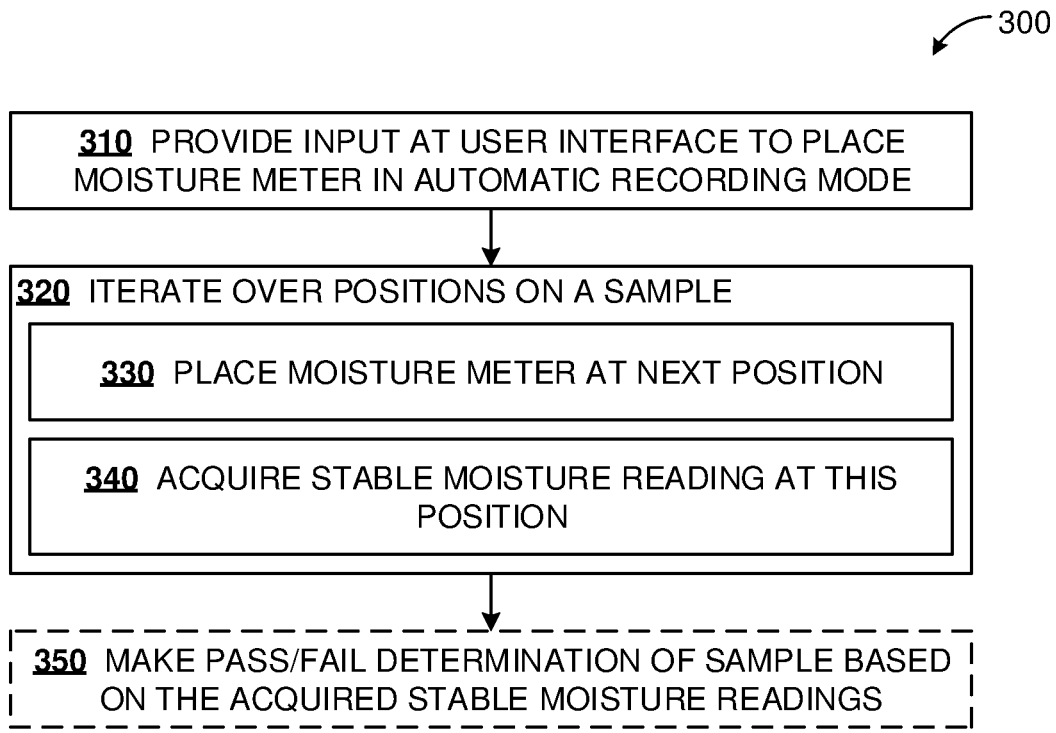
FIG. 3 is a flowchart of an example use case of the disclosed technologies.

FIG. 3 is a flowchart 300 of an example use case of the disclosed technologies. At process block 310, an input is provided at a user interface of a moisture meter to place the moisture meter into an automatic recording mode. At process block 320 an iteration is performed over process blocks 330, 340. The moisture meter is placed at successive positions on a sample, at process block 330, to acquire a corresponding succession of stable moisture readings at process block 340, without further input at the user interface. Moisture readings can be considered stable if they vary by less than a threshold amount over a predetermined time duration. The sample can be wood or concrete, or another material. At optional process block 350, shown dashed, a pass-fail determination of the sample can be made, based on the acquired stable moisture readings. The pass-fail determination can be based on comparing the measurements to a predetermined threshold stored on the moisture meter.

Example Applications

A wide range of applications can benefit from the disclosed technology, a few of which are described herein. In the lumber industry, logs, rough cut planks, and finished material such as 2x4s or plywood sheets all have moisture content which can affect usage, storage, or downstream processing. Often, wood products can be stored outdoors and can be susceptible to moisture penetration from an exposed surface. A series of measurements over a sample (e.g. a log or plywood sheet) can be used to determine whether the sample should be shipped, used, stored for drying, downgraded, or disposed of. Often, a large number of samples need to be tested. The disclosed technologies provide for efficient and user-friendly data acquisition in a production environment, with reduction in operator fatigue and opportunities for human error.

Downstream from lumber operations, finished wood products, such as cabinets, other furniture, musical instruments, or wood flooring, require incoming inspection of wood products used in construction or assembly. Moisture can be a leading cause of warping and other quality issues, and it can be important to sample multiple points to satisfactorily verify the condition of incoming wood.

In another area, concrete commonly hardens within 1-2 days, but can continue to cure and harden for weeks, over which time moisture is gradually lost. Curing times can vary considerably based on concrete formulation, thickness or shape of a pour, or environmental factors. Moisture loss can be non-uniform. In sensitive situations, it can be important to ascertain consistent cure state across a concrete sample before applying a load. All these and numerous other applications can benefit from the disclosed technologies.

Terminology

The usage and meaning of all quoted terms in this section apply throughout this disclosure unless clearly indicated otherwise or repugnant to the context. The terminology below extends to related word forms.

An "alert" is an indication of an abnormal condition, such as a reading that is outside an acceptance band or outside a valid range. Alerts can be provided audibly, visually, haptically, or by a transmitted message, in any combination. An audible alert can be a beep, a tone sequence, a programmable sound, a synthesized or playback voice message. A visual alert can be a lamp, display message, or other display annunciator, and can be pulsed, steady, or flashing. A haptic alert can be a vibration of the moisture meter or associated device. Generally, an alert can be presented directly by the moisture meter, or by an associated computing device such as a smartphone, a wearable appliance, or another portable or stationary computing device. Messages can be sent over a network, e.g. to be logged at a material requirements planning (MRP) enterprise data system.

"Automatic" refers to operations being performed without further inputs at a user interface. The word "automatic" does not preclude other relevant user actions, such as moving a moisture meter from one location to another, nor does it preclude other inputs at a user interface (such as for resetting statistics counters or exiting the automatic recording mode) even while the moisture meter is in an automatic mode.

"Average" refers to an arithmetic mean, or to median, mode, weighted mean, moving average, geometric mean, mid-range value, or any other central measure of a set of measurements, readings, or other numerical values.

"Filtering" and "filter" apply to processes, hardware devices (e.g. utilizing resistors, capacitors, inductors, or operational amplifiers), or software (e.g. executable instructions) for transforming an input signal stream (which can be a continuous signal or a stream of discrete values) into an output signal stream, such that the output stream has certain properties defined by the filter. A low-pass filter can remove high-frequency noise from a signal, producing an output stream that is smoother or more slowly varying than the input stream. A hysteresis filter can apply a threshold or change band to the input stream, such that variations in the input stream above the threshold or outside the change band can be passed on to the output stream, while smaller variations in the input stream are not passed on.

The term "handheld" refers to any device that has a size and weight suitable for being held in a person's hand. Characteristic dimensions of a handheld device can be in the range 1 cm-1 meter and often between 2 cm-20 cm inclusive. Characteristic weights of a handheld device can be in the range 1 g-5 kg and often between 50 g-500 g. The term handheld characterizes a class of device, and does not require that the device actually be held in a person's hand for the disclosed technologies to be used. For example, a handheld moisture meter could be operated by a robotic arm, or mounted on a frame while the sample to be measured is moved along the meter.

"Moisture" or "moisture content" refer to water contained within another material, or the amount thereof. Commonly, moisture content can be reported as percent by weight of the sample, however this is not a requirement, and moisture content can also be reported as an absolute density of the water present. Moisture content can vary both spatially over the sample, and over time.

A "moisture sensor" is a device that can be used to generate a signal dependent on moisture present in the vicinity of the moisture sensor. A moisture sensor can be integrated into a moisture meter. Some example moisture sensors described herein are intended for electrical measurements, however this is not a requirement. The disclosed technologies can be employed with e.g. optical or other types of moisture sensors as well. An electrical moisture sensor can be a combination of two or more electrodes (sometimes, "sensor electrodes") and associated electronics that can make a measurement indicative of moisture. Example moisture sensors can operate on resistive or capacitive principles. A resistive moisture sensor can measure current or resistance between sensor electrodes with voltage applied across the electrodes, or can measure voltage across the electrodes with current driven between the electrodes, in order to determine the resistance between the electrodes (through the sample), which can indicate the moisture content within the sample. A capacitive moisture sensor can measure charging current on a sensor electrode with voltage applied across a pair of sensor electrodes, or can measure voltage with charging current applied, or can measure oscillating frequency of a tank circuit incorporating the capacitance between two sensor electrodes. In one of these ways, or a variation thereof, the capacitance of the sample between sensor electrodes can be determined, which can indicate the moisture content within the sample. The associated electronics can serve to apply a stimulus signal to the sensor electrodes, to filter or amplify a response signal in a circuit incorporating the sensor electrodes, or to digitize the response signal after any filtering or amplification, in any combination. Portions of the associated electronics, such as an analog-to-digital converter (ADC), can be incorporated in a same integrated circuit (IC) as a microprocessor.

A "raw measurement" is a digital value received by a computer processor (e.g. microprocessor or microcontroller) from electronics (e.g. an analog-to-digital converter) servicing a sensor such as a moisture sensor. A measurement can be transformed into a reading of a desired quantity by scaling, calibration, or application of physics equations underlying the sensor operation. Some embodiments can use a system-on-chip (SoC) architecture or a microprocessor IC incorporating an ADC, in which case the raw measurement can be generated within the same physical package as the processor.

A "reading" refers to a value of a measured quantity, particularly moisture content, suitable for presentation to a user or for incorporation into statistics. Typically, a reading can be scaled or calibrated into predefined units. For example, a moisture reading could be 11% calibrated for pine, or 0.08 g/cm$^3$ as an absolute water density.

"Recording" refers to a process of determining and storing a reading, particularly a reading indicative of moisture content. While moisture readings can be stored persistently, i.e. until a group of readings on a sample has been completed or cleared, this is not a requirement. In some embodiments, running sums or histogram counts can be maintained on the fly for subsequent calculations of statistics (such as mean, median, mode, or standard deviation), in which case individual readings may not be further required and can be overwritten.

The term "sample" refers to any material object or entity on which moisture measurements are being made.

A reading is considered "stable" if its variation is less than a threshold amount over a predetermined period of time. In some examples, the threshold amount can be one bit or one unit of a finite precision representation of the reading, meaning that a stable reading is invariant, however this is not a requirement. Thresholds of 2, 4, 5, 8, 10, 16 or some other number of least significant bits (LSBs) can be used. Thresholds can also be expressed as a percentage of a reading can be used, such as 0.1%, 0.2%, 0.5%, 1%, 2%, 5%, or 10% of a current reading or a full-scale reading of the moisture meter. Thresholds can be expressed in units of moisture content, such as 0.2% moisture content referred to pine. In some examples, the predetermined period of time can be one second, however this is not a requirement, and other periods of time from 0.1 s to 50 s can be used. In any event, multiple readings are taken during the period of time used and a determination is made whether each reading is within the threshold amount. If any of the multiple readings are outside the threshold, then the reading is considered unstable and the period of time can be restarted with a new measurement. This process can be repeated until each of multiple readings are within the threshold for the period of time, in which case, the reading is considered stable and is recorded as a valid reading.

"Statistics" refers to aggregate properties of a set of measurements, readings, or other numerical values. Non-limiting examples of statistics include one or more averages, standard deviation, histogram, minimum, maximum, and count (cardinality) of the set of values.

The terms "top," "bottom," and the like are used for convenience, with respect to a common configuration in which a handheld meter can be placed on a top surface of a sample. One of ordinary skill will understand from this disclosure that a choice of actual orientation can be varied without departing from the scope of the disclosed technologies.

Example Method

Figure 4:
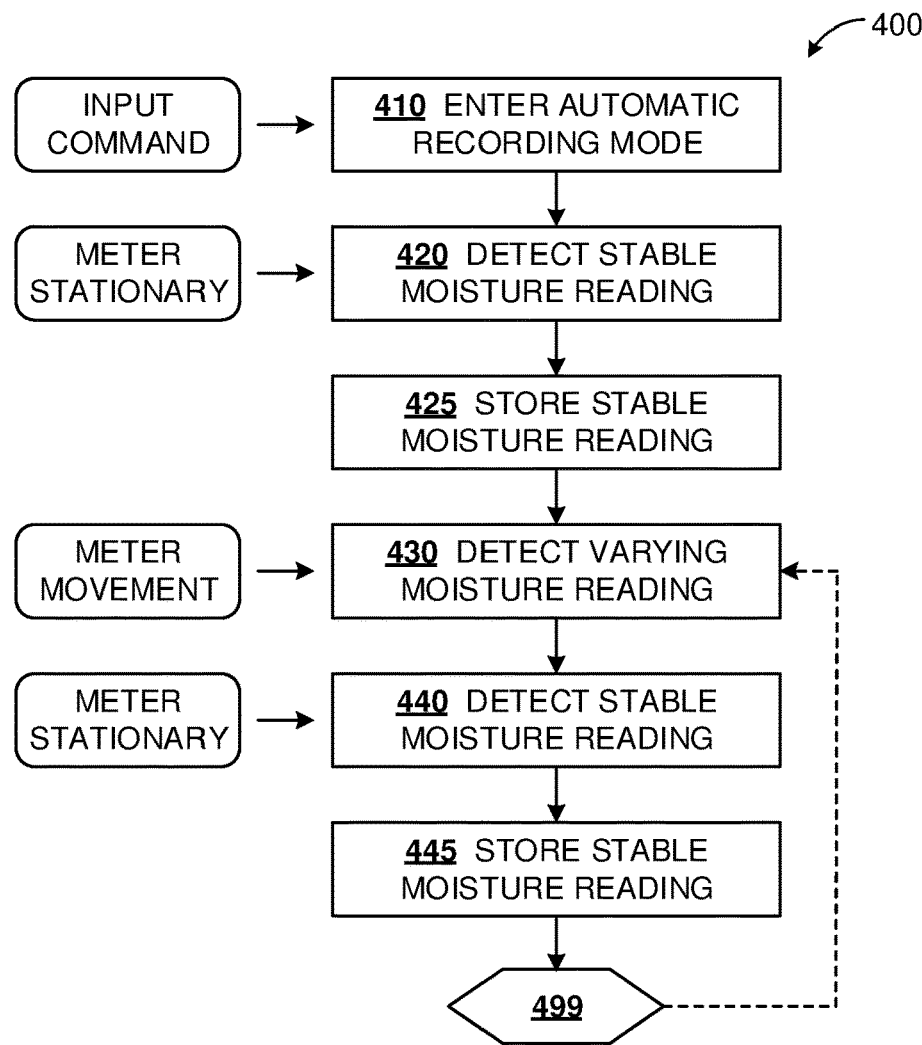
FIG. 4 is a flowchart of an example method according to the disclosed technologies.

FIG. 4 is a flowchart 400 of an example method according to the disclosed technologies. This method describes acquisition of two stable moisture readings with a moisture meter such as 100, and can be performed by a microprocessor or other computing device on board the moisture meter.

At process block 410, the moisture meter can enter an automatic recording mode. This action can be responsive to a received input such as a command (e.g. keypress) from a user. The meter can indicate activation of the automatic recording mode audibly or visibly at a user interface. Having entered the automatic recording mode, and with the moisture meter held steady on a sample, a stable moisture reading can be detected at process block 420 and stored at process block 425. Subsequently, one or more moisture readings varying from preceding readings can be detected at process block 430, indicating that the moisture meter has been moved, for example if the moisture meter is lifted off the sample, or moved across an inhomogeneous sample. In alternate embodiments, movement of the moisture meter can be detected by a sensor such as an accelerometer. With the moisture meter held steady at a second location, the meter reading can revert to stable values. Then, another stable moisture meter reading can be detected at process block 450 and stored at process block 460. A notification of a successful reading can be provided to a user, such as through an audio, visual or haptic feedback. For example, a moisture meter can beep twice to indicate that a stable reading has been recorded, or a user interface lamp or annunciator can be pulsed on.

The flowchart terminates at connector block 499. In some instances, connector block 499 can revert back to process block 430, as shown by dashed line, so that the alternating sequence of detecting varying readings and stable readings can be repeated multiple times. In this manner, locations of abnormal or uneven moisture content can be identified, or uniformity of moisture levels can be confirmed. Readings can be continued as long as a user chooses to leave the moisture meter in an automatic recording mode, or can be continued until a predetermined number of readings have been acquired for batch operation. The meter can also time out and exit the automatic recording mode if no stable readings are acquired over a predetermined timeout period. The stable readings obtained in the automatic recording mode can be stored by the moisture meter.

Example Measurement Loop with Multiple States

Figure 5:
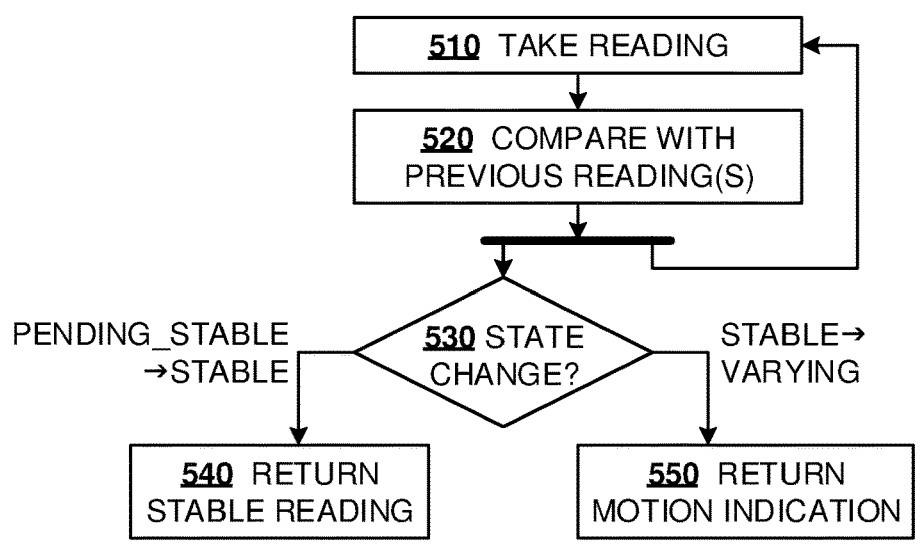
FIG. 5 is a flowchart of an example measurement loop with multiple states, according to the disclosed technologies.

FIG. 5 is a flowchart 500 of an example measurement loop which can be used to obtain moisture readings. At process block 510, a measurement reading can be taken, and at process block 520 this measurement can be compared with one or more immediately preceding readings. Following block 520, the method forks. The right branch loops back to continue taking further measurement readings. The left branch proceeds to process block 530 to detect a change of state.

Entering block 530, the sequence of readings can have three states: Varying, Stable, or Pending_Stable. The stability condition can require readings to vary by less than a threshold amount over a specified duration, which can correspond to N readings. To illustrate, if the specified duration is 1 second, and readings are taken 10 times per second, then N=10. For purposes of discussion, successive readings can be indexed 1, 2, 3, . . . J–N . . . J–2, J–1, J, . . . . The states entering block 530 for reading J can be considered as follows.

Stable State

If all preceding readings from J–N to J–1 were within the threshold amount, then the sequence of readings can already be in a Stable state. If reading J is outside the stability threshold window, then a change of state from Stable to Varying can be detected. The flowchart can follow the "Stable→Varying" branch from block 530 to block 550 and return an indication of a varying moisture reading, which can be regarded as an indication of motion of the moisture meter. Such indication can be used at block 430 of FIG. 4.

Pending_Stable State

If the preceding readings J–1 and J–2 were within the threshold amount, but at least one of the readings from J–N to J–3 was outside the threshold window, then the readings are not varying, but have not remained within the threshold window long enough to satisfy the criterion for stability. This state can be called a Pending_Stable state. A count can be maintained within the Pending_Stable state, indicating a number of consecutive readings within a stability threshold window. If the reading J is within the threshold window, this counter can be incremented. When the counter reaches N (i.e. readings J–N+1 to J all within the threshold window), then the sequence of readings can enter the Stable state. The flowchart can follow the "Pending_Stable→Stable" branch from block 530 to block 540 and return a value of the stable reading. This value can be used at blocks 420 or 440 of FIG.

4. If the incremented counter remains less than N, the sequence of readings can remain in the Pending_Stable state, with no further action.

If the reading J is outside the threshold window, then the sequence of readings can transition to the Varying state, which can end the processing of block 530.

Varying State

If the preceding readings J−1 and J−2 were different by more than the threshold amount, then the sequence of readings can already be in a varying state. If reading J differs from reading J−1 by more than the threshold, then the sequence of readings can remain in a Varying state, and there is no state change. If reading J is within the threshold window with respect to reading J−1, then the reading is no longer varying, but may not have remained within the threshold window long enough to satisfy the criterion for stability. The sequence of readings can enter the Pending_Stable state, the associated counter can be set to two, and processing at block 530 can be terminated.

Variations of flowchart 500 can be implemented. For example, if N=2, the Pending_Stable state can be omitted. Further the rate of taking readings can be varied according to the state. For example, readings can be taken more slowly in the Stable state or in the Varying state to conserve battery life, or readings can be taken at a faster rate in the Pending_Stable rate for increased confidence in detection of a stable reading.

Example Method Extensions

Figure 6:
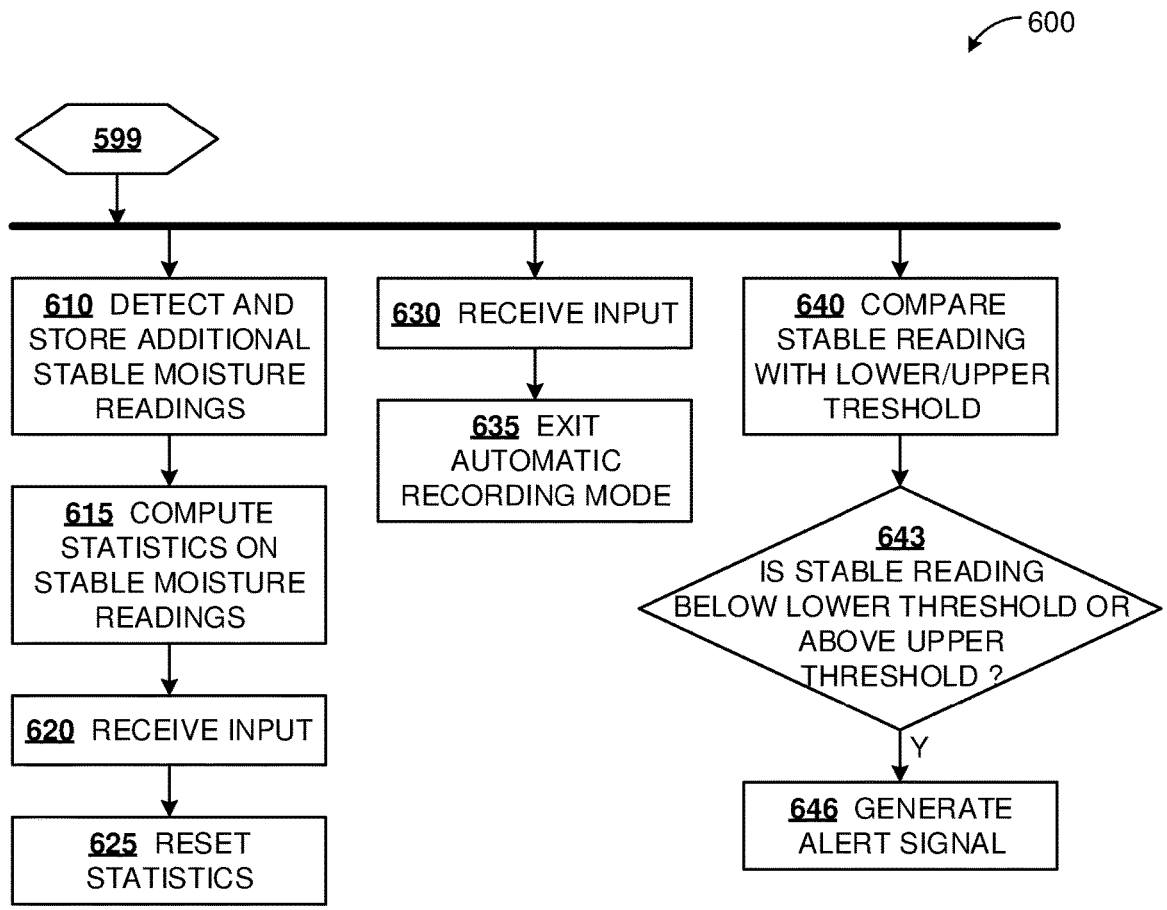
FIG. 6 is a flowchart depicting some extensions of the example method.

FIG. 6 is a flowchart 600 depicting some example extensions of the method of FIG. 4. Starting with connector block 499, such extensions can follow any of several paths as indicated in FIG. 6.

As a first extension, additional stable moisture readings can be detected and stored at process block 610. Statistics can be calculated on the collected stable moisture readings at process block 615. The statistics can include one or more of: minimum, maximum, arithmetic mean, standard deviation, counts above or below a threshold, median, another average, or a histogram. Statistics can be computed or displayed after each stable reading acquired, after completion of a batch of readings, at the time of resetting statistics, or at the time of exiting the automatic recording mode. The statistics can be displayed in response to an input, such as one or more key entries to enter a View Data menu or display mode.

As a further extension, a user input can be received at process block 620 while in the automatic recording mode, as a result of which the statistics can be reset at process block 625. Resetting statistics means that subsequent statistics will be calculated only using stable readings acquired after the reset 625. After a statistics reset 625, the moisture meter can remain in or revert to the automatic reading mode.

As another extension, a user input can be received at process block 630 (which can be distinct from the user input used at process block 625). Based on this input, the moisture meter can exit the automatic recording mode at process block 635. For example, the moisture meter can revert to a manual mode in which a user input is required each time a new reading is to be acquired.

As another extension, a stable reading can be compared with a lower or upper threshold at process block 640. These thresholds can define an acceptable band for moisture content readings for the sample. At process block 643, a determination can be made whether the current stable reading is above the upper threshold in which case an alert signal can be generated at process block 646. Alternatively or additionally, an alert signal can be generated at 646 if the stable reading is found to be below the lower threshold at 643. The lower threshold determination can be cascaded with a comparison with a null threshold: a stable reading below the null threshold can be regarded as a reading in air, discarded with no alert, and not counted in statistics. However, a stable reading above the null threshold but below the lower threshold can be considered as a valid sample moisture reading that is outside the acceptable band. Such a reading can generate an alert, and can also be stored and incorporated into the statistics. That is, only stable readings above a null threshold can be counted towards the statistics.

Example Measurement Loops with Timer

Figure 7:
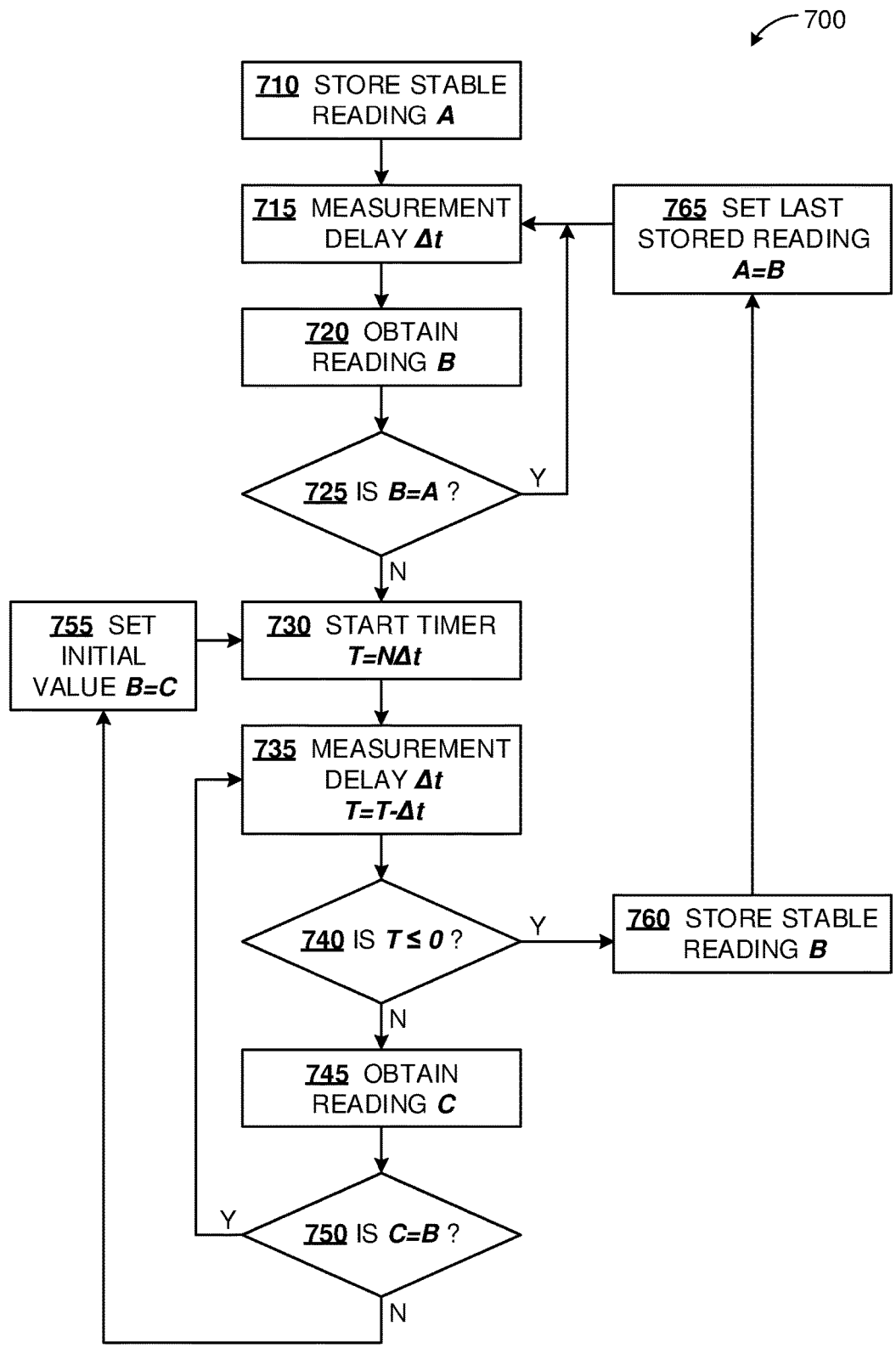
FIG. 7 is a flowchart depicting an example of measurement loops with a timer, according to the disclosed technologies.

FIG. 7 is a flowchart 700 depicting an example method of measurement loops with a timer, according to the disclosed technologies. This method can operate as a continuous procedure with multiple loops. The description of this procedure starts with a stable reading A having been taken and stored, at process block 710. After a measurement interval $\Delta t$ at process block 715, another reading B can be taken at process block 720, and compared with the last stored reading A at decision block 725. As long as the readings B continue to be the same as reading A, the Y branch from decision block 725 can be followed back to block 715, and successive readings B can continue to be taken in a first loop. That is, only one copy of reading A can be stored while the readings remain stable. However, if reading B differs from reading A, then the first loop can terminate, following the N branch from decision block 725.

The different reading B can start a countdown timer at process block 730, set to the amount of time a reading should remain steady in order to be identified as a stable reading, e.g. $T=N \cdot \Delta t$. Reading B can be saved in a temporary register. Then, in a second loop, successive readings C can be taken at process block 745, after respective measurement delays at block 735. These readings can continue while the new reading C matches the initial reading B as tested at decision block 750. That is, the second loop can follow the Y branch from block 750 back to block 735.

The second loop can terminate in two ways. First, if a reading C is different from the initial reading B, then the N branch from decision block 750 can be followed to block 755, so that C can be set to the new initial value for the second loop at process block 755, and the countdown timer can be reset at block 730. Alternatively, the countdown timer can expire, which can be tested at decision block 740 following the delay at block 735. In this case, with all readings C having been the same as initial reading B, the reading B was stable. The Y branch from decision block 740 can be followed, and reading B can be stored at process block 760 as the next stable reading after reading A. Now, the last stable reading can be set to B at block 765, and the first loop can resume at block 715, to wait for a change in value of the reading.

Figure 8:
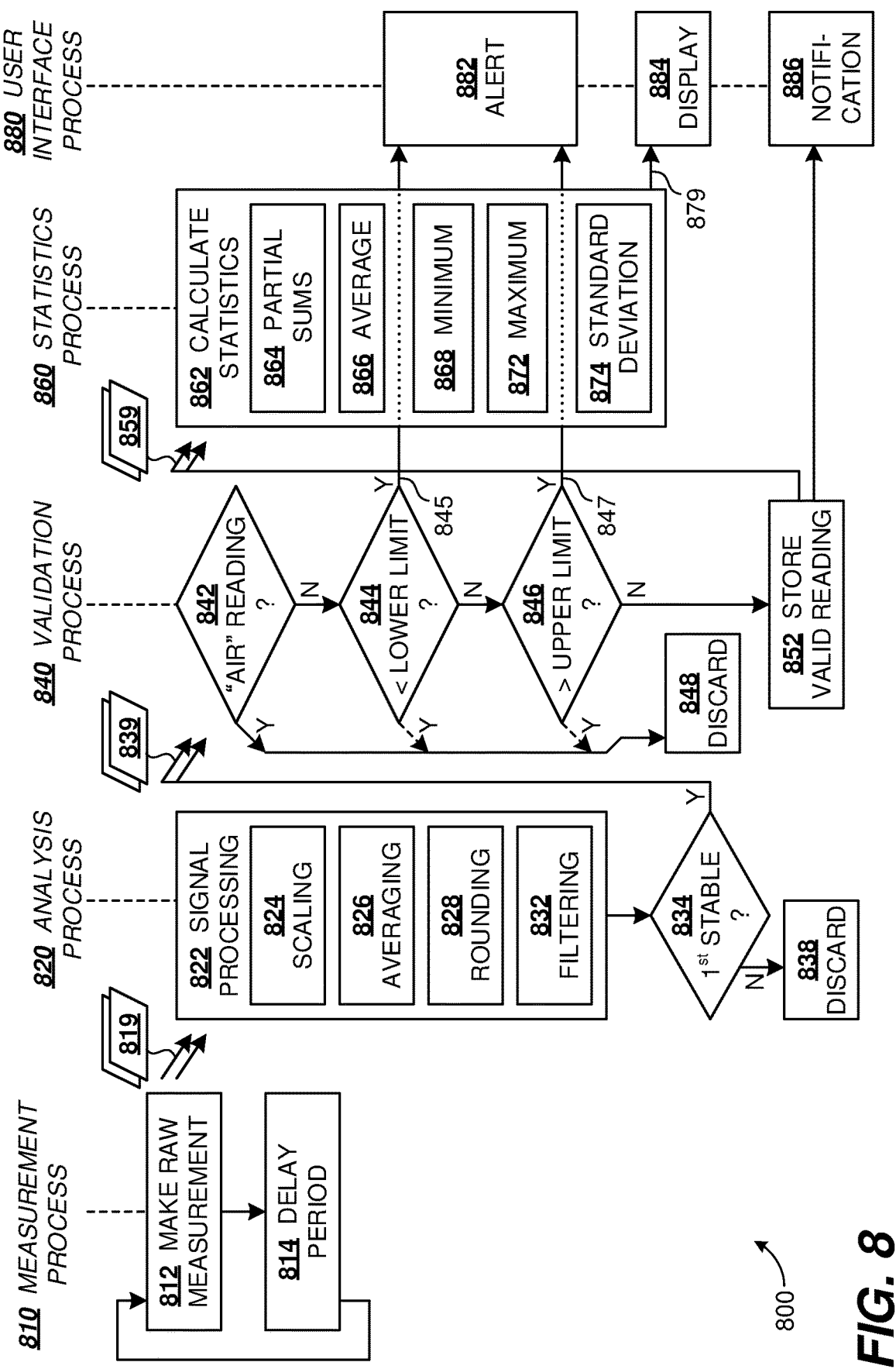
FIG. 8 is a diagram illustrating an example software architecture for implementing disclosed technologies.

The stable readings of process blocks 740, 760, 710 can correspond to the detection of stable readings elsewhere in this disclosure, for example in context of e.g. FIG. 2, 4, or 8. The detection of varying reading at decision block 725 can correspond to the detection of varying reading or an indication of motion elsewhere in this disclosure, such as in context of e.g. FIG. 2 or 4.

Example Software Architecture

FIG. 8 is a diagram illustrating an example software architecture 800 for implementing disclosed technologies. In this example, the software is organized as five processes representing measurements (process 810), analysis (process 820), validation (process 840), statistics (process 860), and user interface (process 880) respectively.

Starting with the measurement process 810, a raw measurement is made at process block 812. After a delay period represented as process block 814, the process returns to process block 812 for another raw measurement. A raw measurement could be, for example, an analog-to-digital (A-to-D) converter reading indicating the amplitude or frequency of a signal obtained by a moisture sensor of the moisture meter in proximity to a sample. In some examples, the repetition rate for raw measurements can be about 10 Hz, corresponding to a delay period 814 of about 0.1 s, however other delay periods from 1 ms to 10 s can be used.

Raw measurements 819 can be transferred from the measurement process 810 to the analysis process 820. In FIG. 8, the double arrows associated with the transferred raw measurements 819 indicate the transfer of data between processes can be asynchronous to none, one, or both of these processes. That is, in some embodiments, each raw measurement can cause the analysis process to be run once. In other embodiments, a group of raw measurements can cause the analysis process to be run once to generate a single moisture reading. In further embodiments, the raw measurements can be transferred and acted upon in batch mode, which can help to preserve battery life of the handheld moisture meter.

Turning to the analysis process 820, raw measurements are processed to obtain stable moisture readings. In signal processing block 822, raw measurements can be scaled at process block 824, averaged at process block 826, rounded or clipped at process block 828, or filtered at process block 832. The scaling at process block 824 can include transforming the measured signal into moisture content according to applicable physics equations, or applying device or material calibrations. The averaging at process block 826 can include a moving average, a running average (e.g. an infinite impulse response filter), a weighted average, or an average over a batch of measurements. The rounding at process block 826 can be to any predetermined finite precision or least count value, and can include clipping, which is equivalent to applying an offset and then rounding. The filtering at process block 832 can include a finite impulse response filter, a low-pass filter, a band-pass filter, downsampling, upsampling, or hysteresis. Although shown as discrete processing blocks, the operations of blocks 824, 826, 828, 832 can be grouped together in one or more software routines.

Then, as moisture readings are obtained as output from the signal processing 822, a determination can be made at decision block 834 whether the moisture readings are stable. The stability determination at process block 834 can be made by comparing a succession of moisture readings obtained from the signal processing 822 with previous readings over a predetermined time period. If these moisture readings are invariant, or vary by less than a threshold amount, a reading can by determined to be stable at decision block 834. Conversely, a moisture reading (output from signal processing 822) that differs from an immediately preceding moisture reading (whether stable or not) by at least a threshold amount can be determined to be a varying reading. The predetermined time period can be 1 second, or in a range 0.1-50 s, 0.2-10 s, or 0.5-2 s.

With reference to FIGS. 4-6 described herein, operations such as those of measurement process 810 and analysis process 820 can be used to detect the stable readings of process blocks 420, 440, or 610, as well as the varying (i.e. not stable) moisture readings of process block 430.

Generally, a series of one or more stable readings can be followed by a series of one or more varying readings, then another series of stable readings, and so on. In order to collect one reading from each measurement location, a first reading in each series of stable readings can be retained, while subsequent stable readings and all variable readings can be discarded. Thus, in addition to detecting whether a reading is stable, process block 834 can distinguish the first stable reading from other readings, following the Y and N branches respectively. A first stable reading 839 in each series of stable readings can be transferred from analysis process 810 to validation process 840 via the Y branch from block 834. Subsequent stable readings of each series, and all varying readings can follow the N branch to be discarded at block 838.

As for the raw measurements 819, the transfer of first stable measurements 839 can be synchronous or asynchronous between the processes 820, 840. Validation process 840 can determine whether a stable reading is valid, invalid, within an acceptance range or outside the acceptance range.

At decision block 842, a current stable reading can be compared with a null threshold to determine whether the reading corresponds to air or to a reading on a sample. If the stable reading is below the null threshold, it can be considered to be an "air" reading, and can be discarded at process block 848 by following the Y branch from decision block 842. If the stable reading is not an air reading, it can be compared with a lower limit at decision block 844. If below the lower limit, the reading can be discarded following the dashed Y branch to block 848. Additionally, a signal can be sent following arrow 845 to alert block 882 of the user interface process, to be described further.

If the stable reading is above the lower limit, the validation process 840 can proceed to decision block 846 where the stable reading can be compared with an upper limit. Similar to handling the lower limit at process block 844, a stable reading above the upper limit can be discarded by following the dashed Y branch to block 848, and an alert can be generated by signaling the alert block 882 via arrow 847. A stable reading below the upper limit can be retained as a valid stable reading for a sample, and can be stored at process block 852. A signal can also be sent to notification block 886 indicating acquisition of a valid reading. In this illustration, the only valid samples stored are those between lower and upper limits. In alternative embodiments, the upper and lower limits can be used to indicate a tolerance band, in which case stable readings can be retained and stored even if they fail the lower or upper limit tests of process blocks 844, 846.

The stable readings 859 can be transferred to statistics process 860 either synchronously or asynchronously for statistics calculations at process block 862. Statistics calculations can include, at process block 864, running tallies of partial sums as stable readings are acquired, which can facilitate computation of mean, standard deviation, or other statistics measures. Other statistics calculations can include average at 866, minimum at 868, maximum at 872, or standard deviation at 874. Output statistics values are communicated from block 862 to display manager block 884 via arrow 879.

Turning to user interface process 880, subprocess block 882 can generate alerts when stable readings are found to be outside a validity or acceptance band. Display manager subprocess 884 can present stable readings or calculated statistics on a display. Notification subprocess 886 can indicate when valid stable readings are acquired. Alerts and notification can be auditory, visual, haptic, or as a transmitted electronic or wireless message, in any combination. Display presentation, alerts, or notifications can be issued from the moisture meter itself, or from an associated auxiliary device such as a smartphone. User interface process 880 can run locally on the moisture meter, or on the associated auxiliary computing device. Similarly, other processes of the software architecture 800 can be distributed between the moisture meter and the associated computing device.

Example Hardware Architecture

Figure 9:
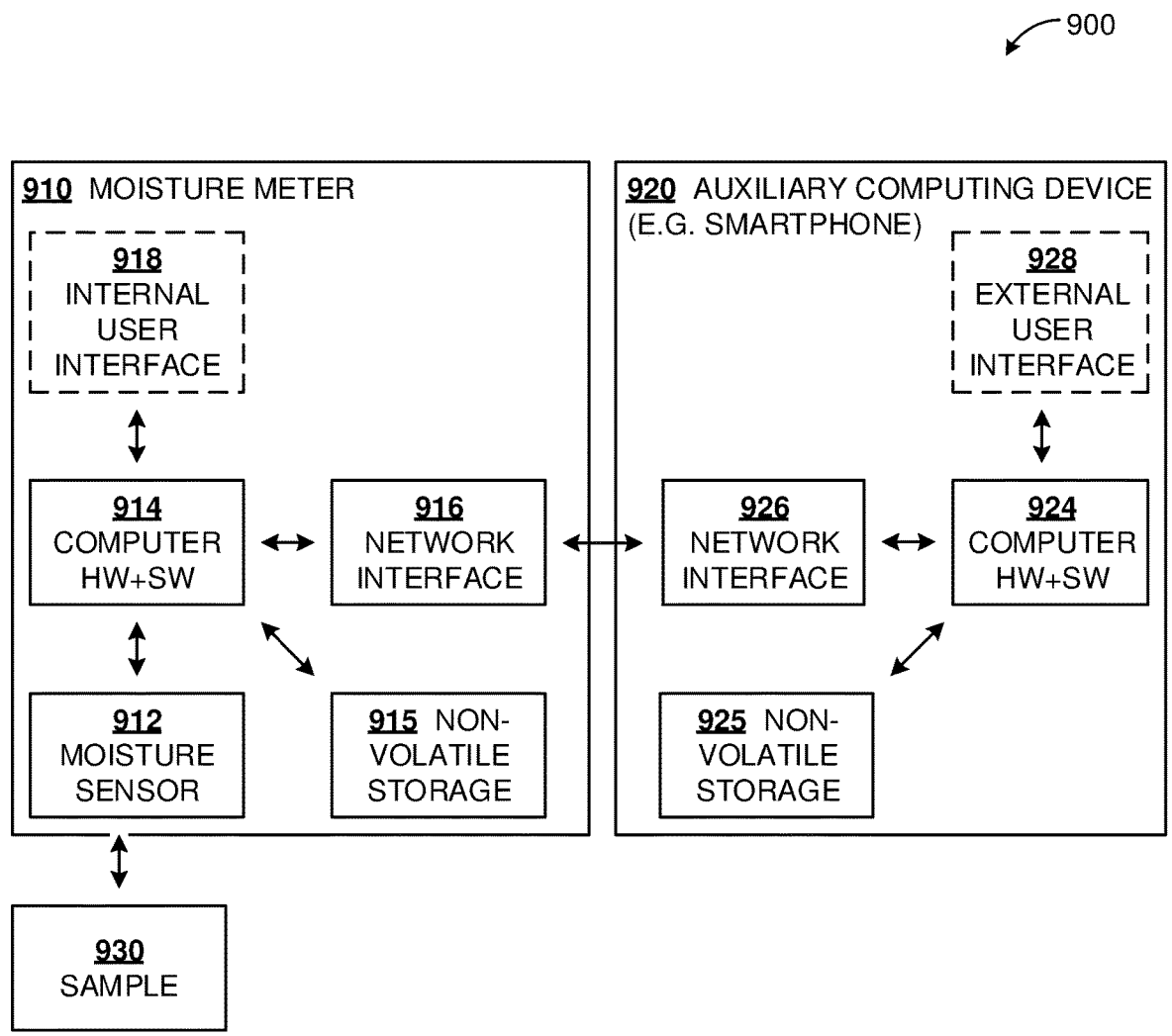
FIG. 9 is a block diagram of an example hardware architecture for implementing disclosed technologies.

FIG. 9 is a block diagram of an example hardware architecture 900 for implementing disclosed technologies. Moisture meter 910 can be similar to that illustrated in FIG. 1, and can incorporate a computer 914 coupled to a moisture sensor 912 and an integrated user interface 918. Moisture sensor 912 can include sensor electrodes and associated electronics to provide a stimulus signal at the sensor electrodes and detect the response with a sample 930 proximate to the sensor electrodes. The user interface 918 can include a keypad similar to 120 and a display similar to 125. The computer 914 can be based on a microprocessor or microcontroller with associated peripherals as described herein or as known in the computer art. For example, digital input/output ports or a peripheral bus can be used to interface with the moisture sensor 912 or with the user interface 918.

In some examples, the moisture meter 910 can include a network interface 916 (such as Bluetooth, Wi-Fi, infrared link, another personal area network, or a proprietary wireless connection) over which the moisture meter 910 can be coupled, directly or indirectly, to an auxiliary computing device 920 having its own network interface 926 and processor 924. Auxiliary computing device 920 can be a smartphone, tablet, portable or fixed computer, television set, or remote control device. In varying examples, the technologies described herein can be implemented wholly on moisture meter 910, or distributed between the moisture meter 910 and auxiliary computing device 920. Particularly, auxiliary computing device 920 can include its own user interface 928 on which readings, statistics, or notifications described herein can be displayed, or from which user input can be provided to control the operations of moisture meter 910. In some examples, internal user interface 918 can be omitted from the moisture meter 910.

Computer 914, incorporating one or more hardware processors, can operate the electronic moisture sensor 912, can communicate with external or internal user interface 918, 928, and/or can execute instructions to perform any of the processes, methods, or variations thereof as described herein. Either moisture meter 910 or auxiliary computer 920 can incorporate non-volatile storage 915, 925 for storing measurements, readings, calibration values, or software associated with the disclosed technologies, as described herein.

Example State Diagram

Figure 10:
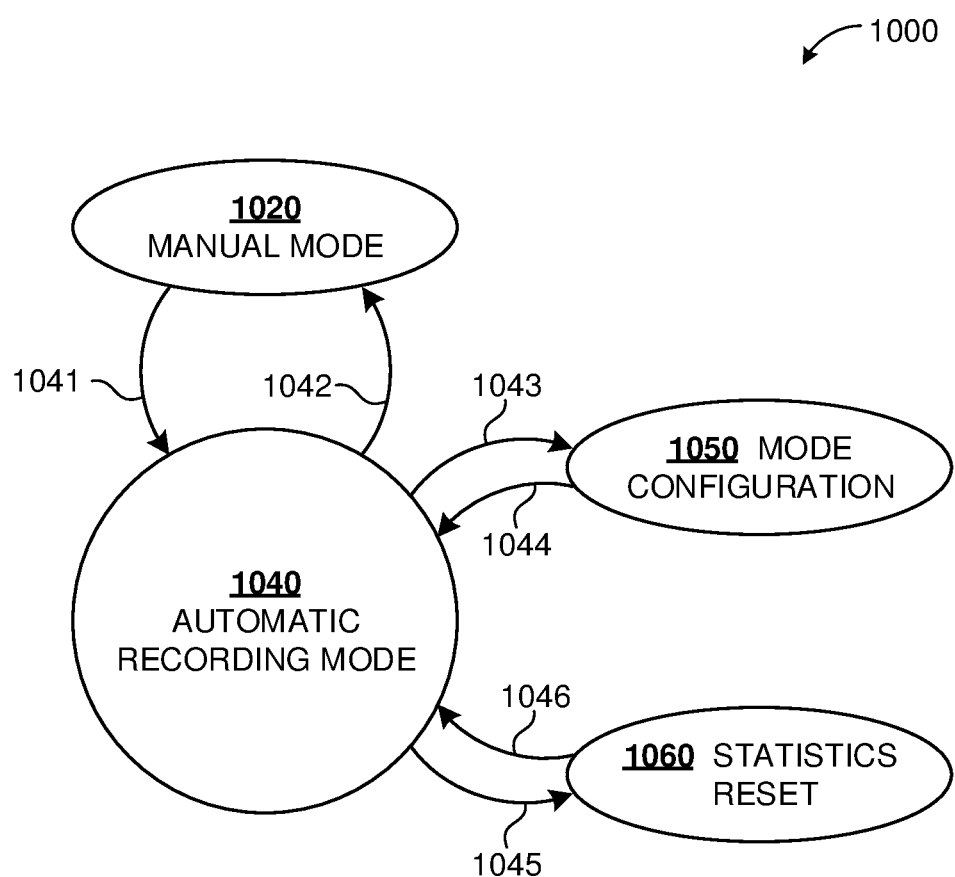
FIG. 10 is an example state diagram illustrating aspects of the disclosed technologies.

FIG. 10 is an example state diagram 1000 illustrating aspects of the disclosed technologies on a handheld moisture meter. State 1020 is a manual mode of operation, while state 1040 is an automatic recording mode as described herein. A user input 1041, such as a keypress, can be used to place a moisture meter into automatic recording mode 1040. Likewise, another user input 1042 can be used to restore the moisture meeting to manual mode 1020.

State 1060 can be accessed to configure the automatic recording mode 1040, for example to select a number of readings to be recorded in a measurement session on a sample, to select the statistics to be computed, or to set alarm limits above or below which an alarm should be indicated. User inputs 1043, 1044 can be used to enter or exit the mode configuration state 1050. Another state 1050 can be used to reset or clear the statistics without exiting the automatic recording mode. Responsive to user input 1045 the moisture meter can enter the statistics reset state 1060. In state 1060, assorted counters (number of events, running total of readings or squares of readings) can be reset (e.g. cleared to zero), following which the moisture meter can revert automatically to the recording mode 1040. An audio or visible notification can indicate entry into or exit from the reset state 1060. In some examples, the moisture meter can undertake transition 1045 automatically, for example upon completion of a batch of automated readings having a predetermined count, such as 3, 4, or any number in the range 5-10, 11-20, or even more.

A Generalized Computer Environment

Figure 11:
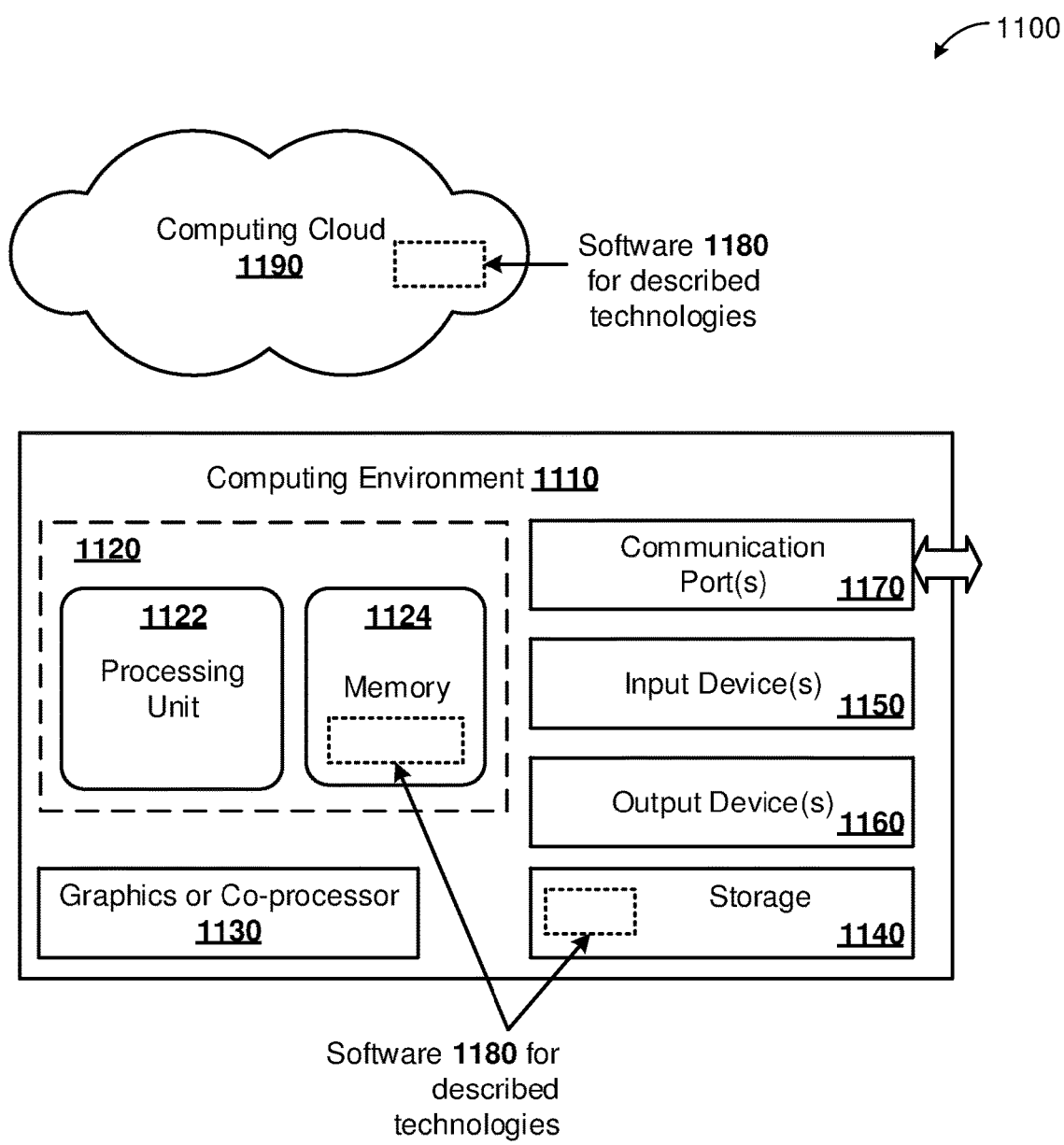
FIG. 11 is a diagram schematically depicting a computing environment suitable for implementation of disclosed technologies.

FIG. 11 illustrates a generalized example of a suitable computing system 1100 in which described examples, techniques, and technologies, including configuration, deployment, or operation, of an automatic recording mode of a moisture meter, can be implemented. The computing system 1100 is not intended to suggest any limitation as to scope of use or functionality of the present disclosure, as the innovations can be implemented in diverse general-purpose or special-purpose computing systems.

With reference to FIG. 11, computing environment 1110 includes one or more processing units 1122 and memory 1124. In FIG. 11, this basic configuration 1120 is included within a dashed line. Processing unit 1122 executes computer-executable instructions, such as for implementing components of a software architecture for automated recording (e.g., components shown in FIG. 8), any of the methods described herein (e.g., illustrated in context of FIG. 4, 6, 10, or 3), or various other architectures, components, data structures, handlers, managers, or modules described herein. Processing unit 1122 can be a general-purpose central processing unit (CPU), a processor in an application-specific integrated circuit (ASIC), or any other type of processor. In a multi-processing system, multiple processing units execute computer-executable instructions to increase processing power. Computing environment 1110 can also include a graphics processing unit or co-processing unit 1130. Tangible memory 1124 can be volatile memory (e.g., registers, cache, or RAM), non-volatile memory (e.g., ROM, EEPROM, or flash memory), or some combination thereof, accessible by processing units 1122, 1130. The memory 1124 stores software 1180 implementing one or more innovations described herein, in the form of computer-executable instructions suitable for execution by the processing unit(s) 1122, 1130.

A computing system 1110 can have additional features, such as one or more of storage 1140 (representing e.g. storage for executable instructions, configuration or state information of a moisture meter), input devices 1150, output devices 1160, or communication ports 1170. An interconnection mechanism (not shown) such as a bus, controller, or network interconnects the components of the computing environment 1110. In some examples, operating system software (not shown) provides an operating environment for other software executing in the computing environment 1110, and coordinates activities of the components of the computing environment 1110.

The memory 1124 or storage 1140 can also store acquired or calculated data, including measurements, readings, or statistics of a moisture meter. The memory 1124 or storage 1140 can also store some or all of a configuration file, an auxiliary input file, and/or other configuration and operational data. The tangible storage 1140 can be removable or non-removable, and includes flash memory, magnetic disks, magnetic tapes or cassettes, CD-ROMs, DVDs, or any other medium which can be used to store information in a non-transitory way and which can be accessed within the computing environment 1110. The storage 1140 stores instructions of the software 1180 (including instructions and/or data) implementing one or more innovations described herein.

The input device(s) 1150 can be a mechanical, touch-sensing, or proximity-sensing input device such as a push-button, keypad, keyboard, mouse, pen, touchscreen, or trackball, a voice input device, a scanning device, or another device that provides input to the computing environment 1110. The output device(s) 1160 can be a display, indicator lamp, printer, speaker, optical disk writer, or another device that provides output from the computing environment 1110.

The communication port(s) 1170 enable communication over a communication medium to another computing entity. The communication medium conveys information such as computer-executable instructions, audio or video input or output, readings, alerts, notifications, or other data in a modulated data signal. A modulated data signal is a signal that has one or more of its characteristics set or changed in such a manner as to encode information in the signal. By way of example, and not limitation, communication media can use an electrical, optical, RF, acoustic, or other carrier.

In some examples, computer system 1100 can also include a computing cloud 1190 in which instructions implementing all or a portion of the disclosed technology can be executed. Any combination of memory 1124, storage 1140, and computing cloud 1190 can be used to store software instructions and data of the disclosed technologies. A local or datacenter computing environment 1110 can utilize the computing cloud 1190 to obtain computing services and perform computing operations (e.g., data processing, data storage, and the like).

In some examples, software embodiments of the disclosed technologies can be deployed on a smartphone, tablet, portable or fixed computer, television set, memory card, memory stick, or a handheld remote control device.

The present innovations can be described in the general context of computer-executable instructions, such as those included in program modules, being executed in a computing system on a target real or virtual processor. Generally, program modules or components include routines, programs, libraries, objects, classes, components, data structures, etc. that perform particular tasks or implement particular data types. The functionality of the program modules can be combined or split between program modules as desired in various embodiments. Computer-executable instructions for program modules can be executed within a local or distributed computing system.

The terms "system", "environment", and "device" are used interchangeably herein. Unless the context clearly indicates otherwise, neither term implies any limitation on a type of computing system, computing environment, or computing device. In general, a computing system, computing environment, or computing device can be local or distributed, and can include any combination of special-purpose hardware and/or general-purpose hardware and/or virtualized hardware, together with software implementing the functionality described herein. Virtual processors, virtual hardware, and virtualized devices are ultimately embodied in one or another form of physical computer hardware.

General Considerations

As used in this disclosure, the singular forms "a", "an", and "the" include the plural forms unless the context clearly dictates otherwise. Additionally, the terms "includes" and "incorporates" mean "comprises". Further, the term "coupled" encompasses mechanical, electrical, magnetic, optical, wireless, as well as other practical ways of coupling or linking items together, and does not exclude the presence of intermediate elements between the coupled items. Furthermore, as used herein, the terms "or" or "and/or" mean any one item or combination of items in the phrase.

The systems, methods, and apparatus described herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed things and methods require that any one or more specific advantages be present or problems be solved. Furthermore, any features or aspects of the disclosed embodiments can be used in various combinations and subcombinations with one another.

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed things and methods can be used in conjunction with other things and methods. Additionally, the description sometimes uses terms like "access," "acquire," "analyze," "apply," "average," "calculate," "calibrate," "clear," "clip," "compare," "compute," "delay," "determine," "digitize," "discard," "display," "downsample," "encode," "enter," "evaluate," "execute," "exit," "filter," "forward," "generate," "identify," "input," "incorporate," "iterate," "measure," "make," "obtain," "output," "place," "process," "provide," "receive," "record," "repeat," "round," "reset," "retain," "retrieve," "run," "scale," "select," "sense," "store," "stream," "transfer," "transform," "transmit," "upsample," "use," "validate," and "weight" to indicate computer operations in a computer system. These terms denote actual operations that are performed by or managed by a computer. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the disclosed methods can be implemented as computer-executable instructions or a computer program product stored on one or more computer-readable storage media, such as tangible, non-transitory computer-readable storage media, and executed on a computing device (e.g., any available computing device, including tablets, smartphones, or other mobile devices that include computing hardware). Tangible computer-readable storage media are any available tangible media that can be accessed within a computing environment (e.g., one or more optical media discs such as DVD or CD, volatile memory components (such as DRAM or SRAM), or nonvolatile memory components (such as flash memory or hard drives)). By way of example, and with reference to FIG. 11, computer-readable storage media include memory 1124, and storage 1140. The term computer-readable storage media or non-volatile storage do not include signals and carrier waves. In addition, the terms computer-readable storage media or non-volatile storage do not include communication ports (e.g., 1170) or communication media.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network, a cloud computing network, or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in Adobe Flash, assembly language, B #, C, C++, C #, Curl, Dart, Fortran, Haskell, Java, JavaScript, Julia, Lisp, Matlab, Octave, Perl, Python, R, Ruby, Rust, SAS, SPSS, SQL, WebAssembly, any derivatives thereof, or any other suitable programming language, or, in some examples, markup languages such as HTML or XML, using CSS, JSON, or any combination of suitable languages, libraries, packages, or scripts. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, infrared, and optical communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A computer-implemented method, comprising:
    at a moisture meter:
        entering an automatic recording mode responsive to a received input and, in the automatic recording mode, performing actions a) through h) without further input at a user interface:
            a) detecting a first stable moisture reading for a predetermined time duration;
            b) storing the first stable moisture reading;
            c) detecting one or more varying moisture readings different from the first stable moisture reading;
            d) detecting a second stable moisture reading for the predetermined time duration;
            e) storing the second stable moisture reading;
            f) detecting one or more additional varying moisture readings different from the second stable moisture reading;
            g) detecting a third stable moisture reading for the predetermined time duration; and
            h) storing the third stable moisture reading;
        wherein action a) precedes c), action c) precedes d), action d) precedes f), and action f) precedes g);
        wherein the first and second stable moisture readings form a pair of successive stable moisture readings, which are separated by the one or more varying moisture readings;
        wherein the second and third stable moisture readings form another pair of successive stable moisture readings, which are separated by the one or more additional varying moisture readings; and
        wherein the one or more varying moisture readings and the one or more additional varying moisture readings are indicative of movement of the moisture meter.

2. The computer-implemented method of claim 1, further comprising:
    detecting and storing additional stable moisture readings while in the automatic recording mode; and
    computing one or more statistics on the first, second, third, and additional stable moisture readings.

3. The computer-implemented method of claim 2, wherein the statistics comprise one or more of: minimum, maximum, arithmetic mean, or standard deviation.

4. The computer-implemented method of claim 2, wherein the received input is a first received input, and further comprising:

resetting the statistics in response to a second received input, while remaining in the automatic recording mode.

5. The computer-implemented method of claim 2, wherein only moisture readings above a threshold are incorporated into the computed statistics.

6. The computer-implemented method of claim 1, wherein the automatic recording mode comprises:
making repetitive periodic raw measurements indicative of moisture proximate to the moisture meter; and
processing the raw measurements to obtain a succession of moisture readings including the first, second, and third stable moisture readings, the varying moisture readings, and the additional varying moisture readings.

7. The computer-implemented method of claim 6, wherein the processing comprises one or more of: averaging, filtering, or rounding.

8. The computer-implemented method of claim 6, wherein the making and the processing are performed continually during the automatic recording mode, without any user input.

9. The computer-implemented method of claim 1, wherein each of the varying moisture readings differs from a respective immediately preceding moisture reading by at least a threshold amount.

10. The computer-implemented method of claim 1, wherein the received input is a first received input, and further comprising:
exiting the automatic recording mode in response to a second received input.

11. The computer-implemented method of claim 1, further comprising:
comparing the first stable moisture reading with a first threshold or a second threshold; and
generating an alert signal if the first stable moisture reading is below the first threshold or above the second threshold.

12. The computer-implemented method of claim 1, further comprising:
generating respective notification signals responsive to the detecting of the first and second stable moisture readings.

13. A non-transitory computer-readable medium storing instructions which, when executed by one or more processors, cause the one or more processors to perform the computer-implemented method of claim 1.

14. A moisture meter comprising:
an electronic moisture sensor;
one or more processors, with memory coupled thereto, configured to operate the electronic moisture sensor, to communicate with a user interface, and to execute instructions comprising:
first instructions to acquire a succession of stable moisture readings in a repetitive loop without input from the user interface;
wherein each of the stable moisture readings is unchanging for at least a predetermined time duration; and
wherein successive pairs of the stable moisture readings are separated by at least one varying moisture reading different from an immediately preceding one of the stable moisture readings, and the at least one varying moisture reading is further indicative of movement of the moisture meter; and
second instructions to compute one or more statistics on the succession of stable moisture readings; and
third instructions to provide the computed statistics to the user interface.

15. The moisture meter of claim 14, wherein the user interface comprises a keypad and a display on the moisture meter.

16. The moisture meter of claim 14, wherein the user interface is part of a computing device coupled to the moisture meter over a network connection.

17. The method of claim 1, wherein a criterion for determining that the first, second, and third stable moisture readings are considered stable is that each varies by less than a threshold amount over the predetermined time duration.

18. The method of claim 1, wherein the first, second, and third stable moisture readings are indicative of moisture levels in a sample, the sample comprising wood or concrete.

19. The method of claim 1, further comprising:
making a pass-fail determination for a sample based at least partly on the first, second, and third stable moisture readings.

* * * * *